US00PP16314P2

(12) United States Plant Patent
Takatomi

(10) Patent No.: US PP16,314 P2
(45) Date of Patent: Mar. 7, 2006

(54) *NEIREMBERGIA* PLANT NAMED 'BLUE EYE'

(50) Latin Name: *Neirembergia hippomanica*
Varietal Denomination: Blue Eye

(75) Inventor: Teruo Takatomi, Aichi (JP)

(73) Assignee: J + H Japan Inc., Aichi (JP)

( * ) Notice: Subject to any disclaimer, the term of this patent is extended or adjusted under 35 U.S.C. 154(b) by 14 days.

(21) Appl. No.: 10/955,386

(22) Filed: Sep. 30, 2004

(51) Int. Cl.
*A01H 5/00* (2006.01)

(52) U.S. Cl. ..... Plt./263
(58) Field of Classification Search ..... Plt./263
See application file for complete search history.

(56) References Cited

U.S. PATENT DOCUMENTS

PP13,934 P2 * 7/2003 Murakami ..... Plt./263
2003/0033649 P1 * 2/2003 Murakami ..... Plt./263

OTHER PUBLICATIONS

UPOV ROM GTITM Computer Database, GTI Jouve Retrieval Software 2005/02 Citation for 'Blue Eye'.*

Huxley, Anthony, ed. *"Nierembergia"* The New Royal Horticultural Society Dictionary Of Gardening vol. 3 L to Q. New York: The Stockton Press: 1992 p. 321.* http://www.naturehills.com/new/product/annualsdetails.aspx?prodid=2325 *Nierembergia* 'Blue Eyes'.*

* cited by examiner

*Primary Examiner*—Kent Bell
*Assistant Examiner*—W. C. Haas
(74) *Attorney, Agent, or Firm*—C. A. Whealy

(57) ABSTRACT

A new and distinct cultivar of *Nierembergia* plant named 'Blue Eye', characterized by its semi-upright to cascading plant habit; freely branching habit; numerous large single flowers that are white in color with purple-colored centers; and good garden performance.

1 Drawing Sheet

Botanical classification: *Nierembergia hippomanica.*
Cultivar denomination: 'Blue Eye'.

BACKGROUND OF THE INVENTION

The present Invention relates to a new and distinct cultivar of *Nierembergia* plant, botanically known as *Nierembergia hippomanica*, and hereinafter referred to by the name 'Blue Eye'.

The new *Nierembergia* is a naturally-occurring whole plant mutation of a proprietary selection of *Nierembergia hippomanica* identified as code number 1121-3, not patented. The new *Nierembergia* was discovered and selected by the Inventor in a controlled environment in Aichi, Japan in April, 1998, from within a population of plants of the parent selection.

Asexual reproduction of the new cultivar by terminal vegetative cuttings since September, 1998, in Aichi, Japan has shown that the unique features of this new *Nierembergia* are stable and reproduced true to type in successive generations.

SUMMARY OF THE INVENTION

Plants of the cultivar Blue Eye have not been observed under all possible environmental conditions. The phenotype may vary somewhat with variations in environment such as temperature and light intensity without, however, any variance in genotype.

The following traits have been repeatedly observed and are determined to be the unique characteristics of 'Blue Eye'. These characteristics in combination distinguish 'Blue Eye' as a new and distinct cultivar of *Nierembergia:*

1. Semi-upright to cascading plant habit.
2. Freely branching habit.
3. Numerous large single flowers that are white in color with purple-colored centers.
4. Good garden performance.

Plants of the new *Nierembergia* are most similar to plants of the parent selection. In side-by-side comparisons conducted in Aichi, Japan, plants of the new *Nierembergia* differed from plants of the parent selection:

1. Plants of the new *Nierembergia* were more uniform in plant habit than plants of the parent selection.
2. Plants of the new *Nierembergia* had larger flowers than plants of the parent selection.

Plants of the new *Nierembergia* can be compared to plants of the cultivar Sunnicobu, disclosed in U.S. Plant Pat. No. 13,934. In side-by-side comparisons plants of the new *Nierembergia* differed from plants of the cultivar Sunnicobu in flower size as plants of the new *Nierembergia* had larger flowers than plants of the cultivar Sunnicobu. In addition, plants of the *Nierembergia* and the cultivar Sunnicobu differed in flower coloration.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new *Nierembergia.*

The photograph at the top of the sheet is a close-up view of typical flower of 'Blue Eye'.

The photograph at the bottom of the sheet comprises a side perspective view of a typical plant of 'Blue Eye' grown in a container.

DETAILED BOTANICAL DESCRIPTION

The aforementioned photographs and following obsevations and measurements describe plants grown in Bonsall, Calif., in an outdoor nursery during the spring under full sun conditions with day temperatures ranging from about 18° C. to about 35° C. and night temperatures ranging from about 7° C. to about 18° C. After planting rooted cuttings, plants were grown for about twelve weeks in 12.5-cm containers. Color references are made to The Royal Horticultural Society Colour Chart, 1995 Edition, except where general terms of ordinary dictionary significance are used.

Botanical classification: *Nierembergia hippomanica* cultivar Blue Eye.

Parentage: Naturally-occurring whole plant mutation of a proprietary selection of *Nierembergia hippomanica* identified as code number 1121-3, not patented.

Propagation:

*Type.*—Vegetative cuttings.

*Time to initiate roots, summer.*—About two to three weeks.

*Time to initiate roots, winter.*—About three to four weeks.

*Root description.*—Fine; white, close to 155D, in color.

*Rooting habit.*—Freely branching.

Plant description:

*Form.*—Annual flowering plant; indeterminate; initially upright, then semi-upright to outwardly spreading and cascading; uniformly mounded plant form. Freely branching habit with about eight primary branches, secondary lateral branches developing potentially at every node. Vigorous growth habit.

*Plant height.*—About 16 cm.

*Plant diameter* (*area of spread*), *single plant.*—About 43 cm.

*Vigor.*—Vigorous; rapid growth rate.

*Lateral branches.*—Length: About 27 cm. Diameter: About 1.5 mm. Internode length: About 8 mm. Texture: Pubescent. Color: 144A.

*Foliage description.*—Arrangement: Alternate; simple; sessile. Length: About 1.5 cm. Width: About 2 mm. Shape: Linear. Apex: Acute. Base: Truncate. Margin: Entire. Texture, upper and lower surfaces: Smooth, glabrous. Venation pattern: Pinnate. Color: Developing leaves, upper and lower surfaces: 146A. Fully expanded leaves, upper and lower surfaces: 146A. Venation, upper and lower surfaces: 146A.

Flower description:

*Flower type and habit.*—Single salverform flowers; flowers face mostly upward or outward; terminal and axillary. Freely flowering habit, about 18 open flowers and about 20 flower buds per primary lateral branch. Flowers not fragrant.

*Natural flowering season.*—Spring though Autumn in Bonsall, Calif.; flowering continuous during this period. Flowers persistent.

*Flower longevity on the plant.*—About seven to ten days.

*Flower size.*—Diameter: About 2.8 cm. Height: About 2.5 cm. Tube length: About 2 cm. Throat diameter, distal end: About 4 mm. Tube diameter, proximal end: About 1 mm.

*Flower buds.*—Length: About 1.5 cm. Diameter: About 4 mm. Shape: Elongated oblong. Color: 157A.

*Petals.*—Quantity/arrangement: About five petals fused in a single whorl, funnelform; slender corolla tube. Length from throat: About 1.2 cm. Width: About 1.5 cm. Shape: Roughly fan-shaped, rounded. Apex: Rounded. Margin: Entire; reflexing at apices. Texture, upper and lower surfaces: Smooth, satiny. Color: When opening, upper surface: Ground color, 85D; towards the base, 85A to 85B; center, 12B. When opening, lower surface: 85D. Fully opened, upper surface: Ground color, 155D; towards the base, 84A to 84B; center, 12B. Fully opened, lower surface: 155D. Flower throat (inside): 12B. Flower tube (outside): 157A.

*Sepals.*—Arrangement/appearance: Single whorl of five sepals fused at base, star-shaped. Length: About 6 mm. Width: About 2 mm. Shape: Linear. Apex: Acuminate. Margin: Entire. Texture, upper and lower surfaces: Smooth, glabrous. Color, upper and lower surfaces: 147B.

*Peduncles.*—Length: About 8 mm. Width: Less than 1 mm. Angle: About 45° from the stem. Strength: Strong. Texture: Pubescent. Color: 146B.

*Reproductive organs.*—Stamens: Quantity per flower: About five. Anther shape: Oval. Anther length: About 1 mm. Anther color: 6B. Pollen amount: Scarce. Pollen color: 6A. Pistils: Quantity per flower: One. Pistil length: About 1.7 cm. Style length: About 1.4 cm. Style color: 145D. Stigma shape: Anvil-shaped. Stigma color: 145A. Ovary color: 146B.

*Seed/fruit.*—Seed and/or fruit production has not been observed.

Disease/pest resistance: Plants of the new *Nierembergia* have not been noted to be resistant to pathogens or pests common to *Nierembergia*.

Garden performance: Plants of the new *Nierembergia* have been observed to have good garden performance. Plants of the new *Nierembergia* have been noted to tolerate temperatures from 0 to 40° C. and have excellent tolerance to rain and wind.

It is claimed:

1. A new and distinct cultivar of *Nierembergia* plant named 'Blue Eye', as illustrated and described.

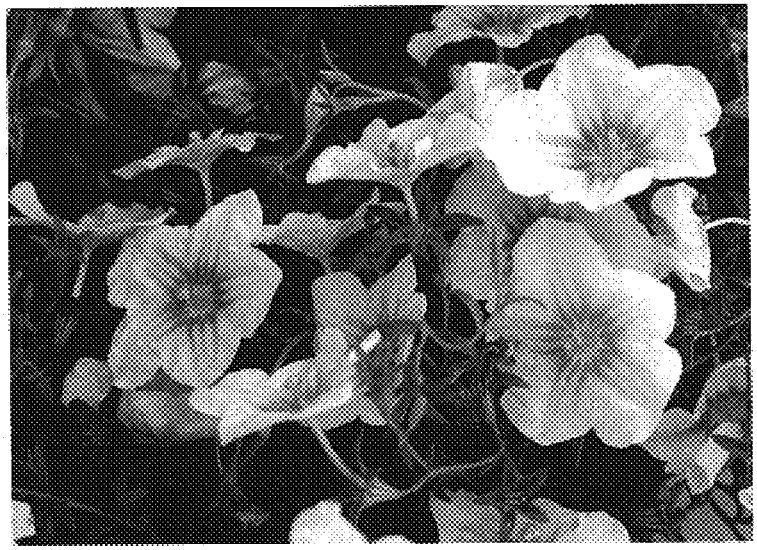
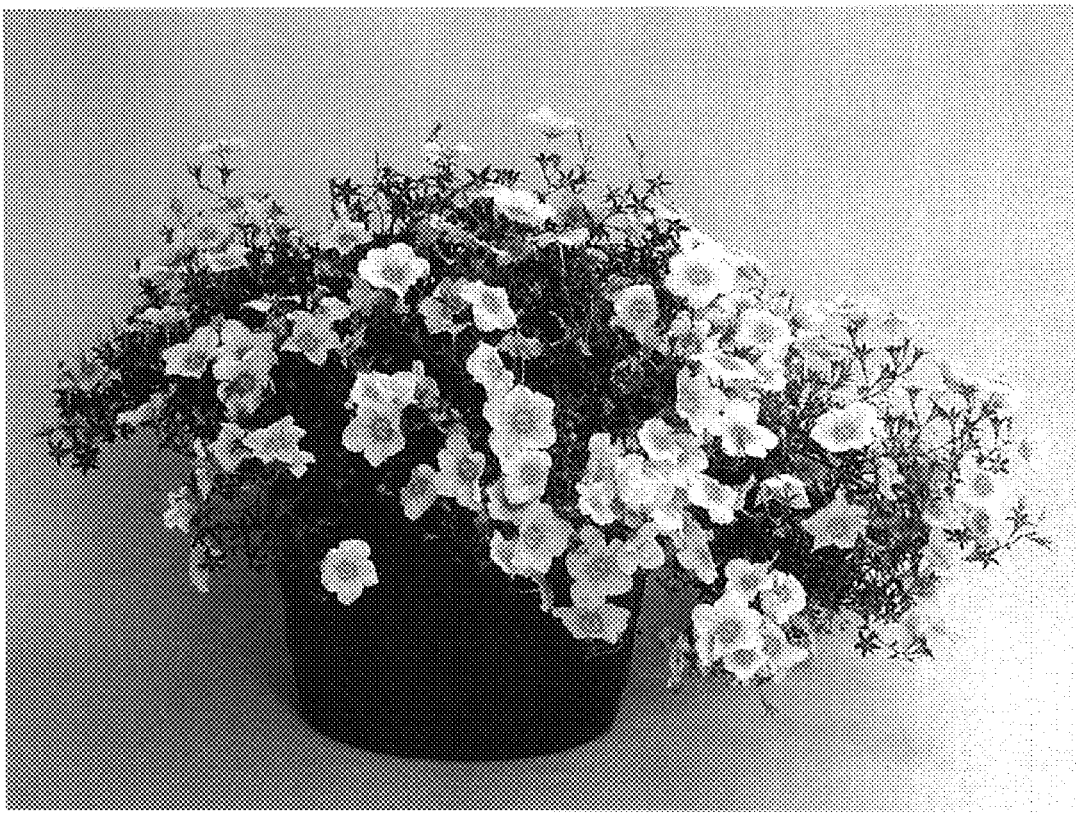

* * * * *